United States Patent
Hong et al.

(10) Patent No.: US 7,560,289 B2
(45) Date of Patent: Jul. 14, 2009

(54) METHODS OF QUANTITATIVELY MEASURING BIOMOLECULES

(76) Inventors: Chin-Yih Rex Hong, 4F., No. 31, Lane 57, Ta Tze St., Ta Tze, Taipei (TW) 104; Herng-Er Horng, 4F., No. 31, Lane 57, Ta Tze St., Ta Tze, Taipei (TW) 104; Chau-Chung Wu, 2F., No. 9, Lane 74, Aiguo E. Rd., Jhongjheng District, Taipei (TW) 100; Hong-Chang Yang, 4F., No. 31, Lane 57, Ta Tze St., Ta Tze, Taipei (TW) 104; Shieh-Yueh Yang, 12F., No. 427, Siyuan Rd., Sindian City, Taipei County (TW) 231

( * ) Notice: Subject to any disclaimer, the term of this patent is extended or adjusted under 35 U.S.C. 154(b) by 466 days.

(21) Appl. No.: 11/164,275

(22) Filed: Nov. 16, 2005

(65) Prior Publication Data

US 2007/0111330 A1 May 17, 2007

(51) Int. Cl.
*G01N 33/553* (2006.01)
*G01N 33/543* (2006.01)

(52) U.S. Cl. ............ 436/526; 436/518; 436/529; 436/538; 436/169

(58) Field of Classification Search ............ 436/518, 436/526, 529, 538, 169
See application file for complete search history.

(56) References Cited

U.S. PATENT DOCUMENTS 5,256,541 A * 10/1993 Pouletty et al. ............ 435/7.24

6,825,655 B2 * 11/2004 Minchole et al. ............ 324/204
2003/0092029 A1 * 5/2003 Josephson et al. .............. 435/6

OTHER PUBLICATIONS

Article titled "Preparation and properties of superparamagnetic nanoparticles with narrow size distribution and Biocompatible" jointly authored by Jiang et al., Jorunal of Magnetism and Magnetic Materials 283 (2004), pp. 210-214.
Article titled "LTS Squid gradiometer system for in vivo magnetoreluxometry" jointly authored by Warzemann et al., Supercond. Sci. Tehnol. 12 (1999), pp.953-955.
Article titled "Nanomagnetic Particles for Squid-Based Magnetically Labeled Immunoussay" jointly authored by Horng et al., IEEE Transactions On Applied Superconductivity vol. 15, No. 2, Jun. 2005, pp. 668-671.

* cited by examiner

*Primary Examiner*—Mark L Shibuya
*Assistant Examiner*—Pensee T Do
(74) *Attorney, Agent, or Firm*—Jianq Chyun IP Office (57) ABSTRACT

The present invention is directed to methods for quantitatively measuring biomolecules by using magnetic nanoparticles. Through the use of the magnetic nanoparticles and the bioprobes coated to the magnetic nanoparticles, the biomolecules conjugated with the bioprobes result in the formation of particle clusters. By measuring the changes in magnetic properties resulting from the existence of the bio-targets, the amount of the bio-targets in a sample to be tested can be measured.

9 Claims, 8 Drawing Sheets

METHODS OF QUANTITATIVELY MEASURING BIOMOLECULES

BACKGROUND OF THE INVENTION

1. Field of the Invention

The present invention generally relates to a method for measuring biomolecules. In particular, the present invention relates to methods for quantitatively measuring biomolecules by using magnetic nanoparticles.

2. Description of Related Art

Nanoparticles in the past were mainly studied because of their size-dependent physical and chemical properties. However, as nanotechnology advances rapidly, further biological or medical applications of nanoparticles have been investigated. Potential applications of nanoparticles to biology or medicine include drug and gene delivery, labeling and detection of biomolecules, separation and purification of biological molecules and cells and Magnetic Resonance Imaging (MRI) contrast enhancement.

Because nanoparticles exist in the same size level as proteins or other biomolecules, magnetic nanoparticles are suitable to be used for tagging or labeling purposes. In order to interact with biological targets, a coating layer (or surfactant) acting as a bioinorganic interface should be attached to the nanoparticle. Besides, an additional layer of linker molecules is required for further functionality. The linker molecule usually has reactive groups at both ends for attaching the linker to the nanoparticle surface and binding various moieties like antibodies, or dyes or fluorophores, respectively. In general, the nanoparticle need to be applied along with optical or coloring agents, so that the nanoparticles interacted with biological targets can be detected. However, further processing steps or preparation procedures are required for linking the optical or coloring agents, and extra manual labor and costs are needed for the application of magnetic nanoparticles.

SUMMARY OF THE INVENTION

Accordingly, the present invention is directed to methods for quantitatively measuring the analytes in the sample by using magnetic nanoparticles.

The present invention is directed to methods for quantitatively measuring biomolecules by using magnetic nanoparticles. Through the use of the magnetic nanoparticles and the bioprobes coated to the magnetic nanoparticles, the biomolecules conjugated with the bioprobes result in the formation of particle clusters and differences between magnetic properties of free magnetic nanoparticles and particle clusters can be measured for determining the amount of the biomolecules.

According to another embodiment of the present invention, a method for measuring an amount of biomolecules in a sample is proposed, comprising: providing a solution having magnetic nanoparticles; coating bioprobe molecules to the surfaces of the magnetic nanoparticles in the solution; measuring the magnetic relaxation time of the solution to determine the amount of the biomolecules.

According to one embodiment of the present invention, a method for measuring an amount of biomolecules in a sample is proposed, comprising: providing a solution having magnetic nanoparticles; coating bioprobe molecules to the surfaces of the magnetic nanoparticles; adding the solution to the sample containing biomolecules to be detected, so that the biomolecules in the sample conjugate with the bioprobe molecules and the nanoparticles agglomerate to form particle clusters; filtrating the solution to obtain the particle clusters; and measuring a saturated magnetization of the particle clusters to obtain the amount of the biomolecules.

According to another embodiment of the present invention, a method for measuring an amount of biomolecules in a sample is proposed, comprising: providing a solution having magnetic nanoparticles; coating bioprobe molecules to the surfaces of the magnetic nanoparticles in the solution; measuring the ac magnetic susceptibility of the solution before and after adding a sample containing the biomolecules to be detected to the solution, so as to obtain an ac magnetic susceptibility reduction or a normalized ac magnetic susceptibility reduction to determine the amount of the biomolecules.

Because the measuring methods proposed in this invention are performed by measuring magnetic properties of the magnetic nanoparticles and/or the formed particle clusters, no fluorescence labels or coloring agents are required for determining the amount of the biomolecules (analytes) in the sample. Hence, no extra processing steps and less human labor are needed and the costs of the test assays can be reduced.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Reference will now be made in detail to the present preferred embodiments of the invention, examples of which are illustrated in the accompanying drawings. Wherever possible, the same reference numbers are used in the drawings and the description to refer to the same or like parts.

The present invention proposes a variety of methods of quantitatively measuring biomolecules in a sample by using magnetic nanoparticles. The basic principles of the measuring methods proposed in this invention are based on the relaxation time, the saturated magnetization and/or the alternating current (ac) magnetic susceptibility reduction.

For the method based on the relaxation time, it can be principally classified as the following steps: providing a solution having magnetic nanoparticles; coating bioprobe molecules to surfaces of the magnetic nanoparticles in the solution; adding a sample containing the biomolecules to be detected to the solution, so that the biomolecules in the sample conjugate with the bioprobe molecules; and measuring a free induction decay (FID) signal of the solution after adding the sample under an external magnetic field, so as to obtain a magnetic relaxation time of un-conjugated magnetic nanoparticles in the solution from the FID signal to determine the amount of the biomolecules.

For the method based on saturation magnetization, it can be principally classified as the following steps: providing a solution having magnetic nanoparticles; coating bioprobe molecules to the surfaces of the magnetic nanoparticles; adding the solution to the sample containing biomolecules to be detected, so that the biomolecules in the sample conjugate with the bioprobe molecules and the nanoparticles agglomerate to form particle clusters; filtrating the solution to obtain the particle clusters; and measuring the saturated magnetization of the particle clusters to obtain the amount of the biomolecules.

For the method based on the alternating current (ac) magnetic susceptibility reduction, it can be principally classified as the following steps: providing a solution having magnetic nanoparticles; coating bioprobe molecules to the surfaces of the magnetic nanoparticles in the solution; measuring the ac magnetic susceptibility of the solution before and after adding a sample containing the biomolecules to be detected to the solution, so as to obtain an ac magnetic susceptibility reduction or a normalized ac magnetic susceptibility to determine the amount of the biomolecules.

Certain aspects of the above steps will be explained in more details in the following paragraphs.

Preparation of the solution having magnetic nanoparticles coated with bioprobes. Herein, $Fe_3O_4$ nanoparticle is used as an example of the magnetic nanoparticle for the present invention; however, other possible magnetic nanoparticles may also be utilized and be comprised within the scope of this invention. A ferrite solution containing $Fe^{2+}$ and $Fe^{3+}$ in 1:2 stoichiometric ratio (molar ratio), was mixed with water containing polar molecules. The polar molecule acts as a surfactant for helping dispersing the $Fe_3O_4$ particles in water or alternatively for improving binding of the bioprobes to the surface of the $Fe_3O_4$ particles. For example, the surfactant can be dextran. However, other possible surfactant may also be utilized and be comprised within the scope of this invention. Hydroxide ions (OH—) were then added to the mixture for adjusting the pH value to around 9-11 to form black $Fe_3O_4$ nanoparticles. Aggregates and excess unbound surfactants were removed and the obtained solution comprising $Fe_3O_4$ nanoparticles is referred as the magnetic fluid. The hydrodynamic diameter of the $Fe_3O_4$ particles was controlled to be between 25 nm to 90 nm by adjusting the initial pH value or other parameters. Then, bioprobes were added to the solution and bound with the oxidized surfactants on the surface of the $Fe_3O_4$ particles with the assistance of $NaIO_4$, so as to prepare the $Fe_3O_4$ particles coated with the bioprobes. Afterwards, the unbound bioprobes were removed from the solution. Hence, the solution containing magnetic particles coated with the bioprobes is obtained.

Afterwards, the solution that contains magnetic particles coated with the bioprobes is used for detecting the conjugated bio-targets or measuring the amount of bio-targets existing in a sample to be tested, by adding the sample to the solution. The choice of the used bioprobes may vary depending on the bio-targets to be detected. According to this invention, the bioprobes will bind or conjugate with the bio-targets to be detected. Because the bioprobes conjugate with bio-targets to be detected, the $Fe_3O_4$ particles may aggregate as clusters through the conjugation of bioprobes-and-bio-targets. In this embodiment, for example, the bioprobe is biotin and the conjugated bio-target is avidin. Usually, one avidin molecule can be conjugated with at most four biotin molecules.

In Table I, examples of possible bio-targets and corresponding bioprobes, as well as the surfactants are lists for the magnetic $Fe_3O_4$ nanoparticles. However, a variety of biomolecules and corresponding conjugates thereof can be used in this invention as long as suitable affinity may be established between the conjugated or binding pair, and the scope of this invention will not be limited by the listed examples. For example, the biomolecule to be tested or measured may be a protein, polysaccharides, a lipoprotein or a glycoprotein, while the bioprobe can be corresponding monoclonal or polyclonal antibodies, biotinylated antibodies or their natural/artificial conjugates. Potential applications of the conjugated pair (bio-targets and corresponding bioprobes), including diagnosis, identification, or cure of tumor, cancer, acute injury or infections or detection or measurement of biomolecules are also listed in Table 1. It should be noted that the either one of the conjugated pair (bio-targets and bioprobes) listed in the table can be coated onto the surface of the magnetic nanoparticles for detecting the other of the conjugated pair. The biotin-avidin pair is used as an example herein to demonstrate the feasibility of the measuring methods of this invention.

TABLE I

Examples of potential bio-targets and corresponding bioprobes, as well as the surfactants for the magnetic $Fe_3O_4$ nanoparticles

| Category of application | Bio-target | Bioprobe | Surfactant |
| --- | --- | --- | --- |
| Tumor | Carcinoembryonic Antigen (CEA) | Anti-CEA | Polyglutamic acid-lysine-tyrosine |
|  | α-fetoprotein (AFP) | Biotinyl-Anti-AFP | Dextran |
| Acute injury or infection | Vascular cell adhesion molecule-1 (VACM-1) | Biotinyl-Anti-VCAM-1 | Dextran |
|  | HBc | Biotinyl-Anti-HBc | Dextran |
|  | C-reactive protein (CRP) | Anti-CRP | Dextran |
| Others | Avidin | Biotin | Dextran |
|  | IgG | Protein A | Dipalmitoyl phosphatidylcholine (DPPC) |

Figure 1:
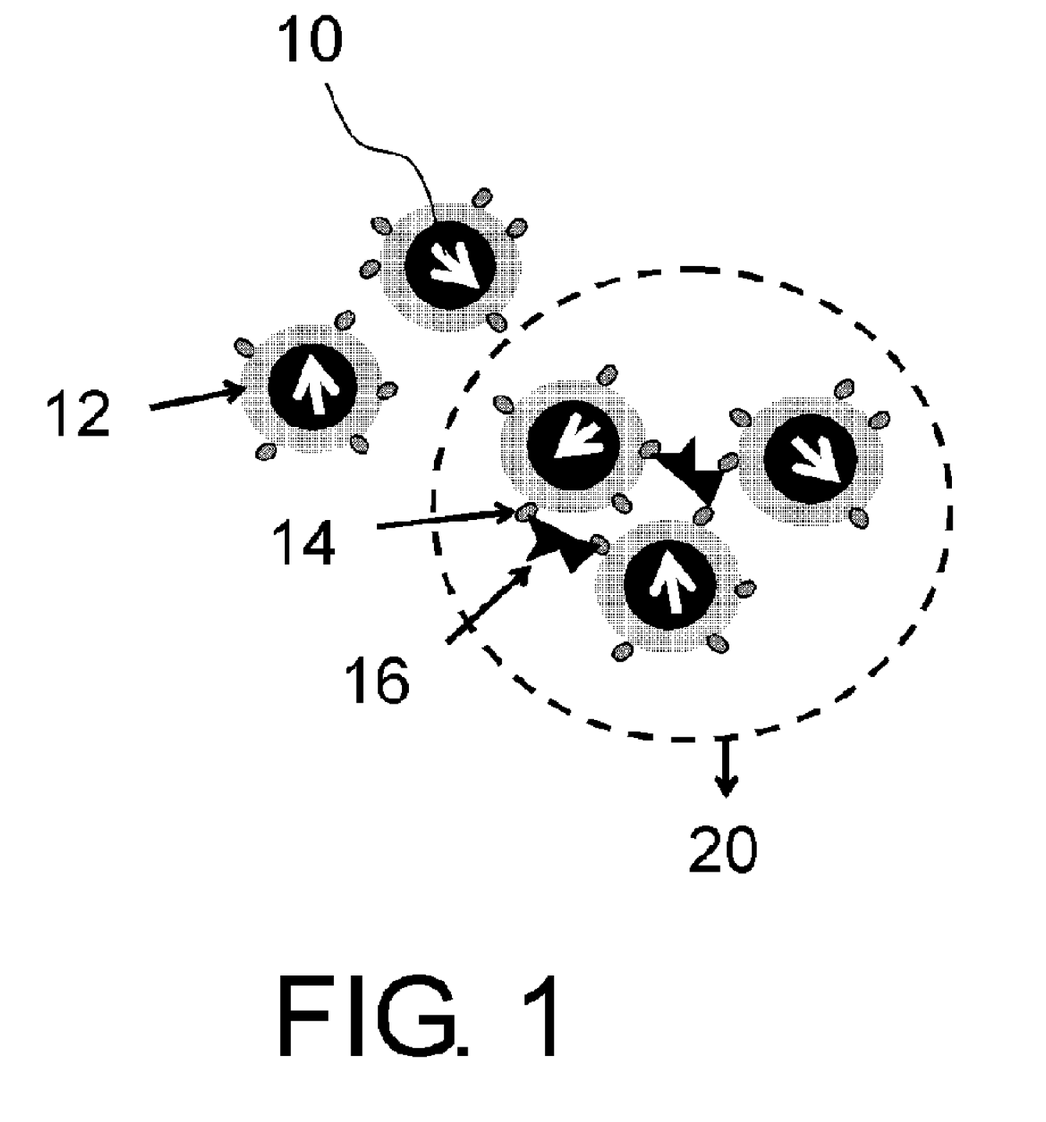
FIG. 1 is a schematic model for the agglomeration of the magnetic nanoparticles.

FIG. 1 is a schematic model for the agglomeration of the magnetic nanoparticles. As shown in FIG. 1, the surfaces of magnetic nanoparticles 10 are coated with surfactants 12 and bioprobes 14. For example, the surfactant 12 is dextran and the bioprobe 14 is biotin. Due to the conjugation of the bioprobes 14 on the magnetic nanoparticles 10 with the added/detected bio-targets 16, a portion of the magnetic nanoparticles 10 agglomerate to form magnetic nanoparticle clusters 20 (circled with dotted line in FIG. 1). For example, the bio-target 16 is avidin. The relaxation time for the free, single magnetic nanoparticles 10 is in the range of $10^{-4}$-$10^{-6}$ seconds, depending on the particle size and concentration, while the relaxation time for the agglomerated particle clusters 20 is in the range of $10^{-3}$ seconds or longer. As more bio-targets 16 are added into the magnetic fluid, more magnetic nanoparticles agglomerate to form particle clusters 20 (i.e. more particle clusters 20). Thus, less free, single magnetic nanoparticles are remained in the solution. Accordingly, the relaxation time counted for the remained single magnetic nanoparticles in the magnetic fluid varies.

Figure 2A:
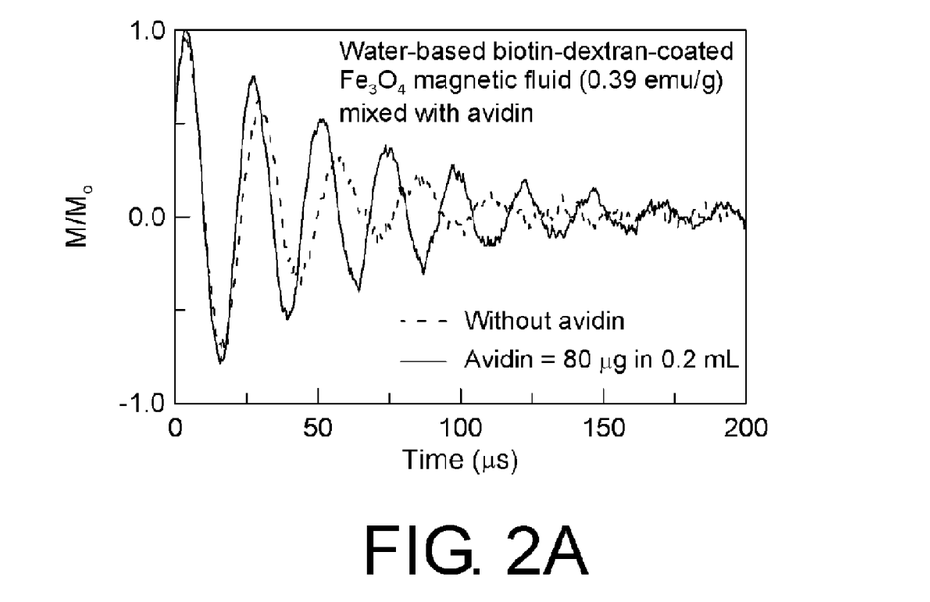
FIG. 2A shows the normalized magnetization $M/M_o$ of the magnetic fluid over the time.

For the measuring method based on the relaxation time, the nuclear magnetic resonance free induction decay (NMR FID) signals of the bioprobe-coated magnetic fluid (0.39 emu/g) are measured before adding any bio-targets and after adding a fixed amount of avidin (80 μg in 0.2 ml). As shown in FIG. 2A, the normalized FID curves (measured magnetization over the acquisition time) of the magnetic fluid before adding avidin (without avidin) or after adding avidin are quite different. Because the magnetic relaxation time of free single magnetic nanoparticles under an external magnetic field can be obtained from the acquired FID signals, different relaxation times are obtained from different FID curves of the magnetic fluid with or without avidin. In this embodiment, a NMR spectrometer using a resonant frequency of 15.4 MHz and an external magnetic field of 3600 G is used for measuring the NMR FID signals, for example. However, any suitable NMR spectrometer can be used depending on the actual requirements. In addition, the relaxation time measured could be spin-lattice relaxation time ($T_1$), spin-spin relaxation time ($T_2$), or inhomogeneous spin-spin relaxation time ($T_2^*$), depending on the detection direction and the uniformity of the external magnetic field. The relaxation time constant in the decay of transverse magnetization considering the combination of molecular interactions (a pure $T_2$ molecular effect) and un-uniformity in the external magnetic field (an inhomogeneous $T_2$ effect) is called $T_2$ star and is given the symbol $T_2^*$. In this embodiment, an example of measuring $T_2^*$ is given.

Figure 2B:
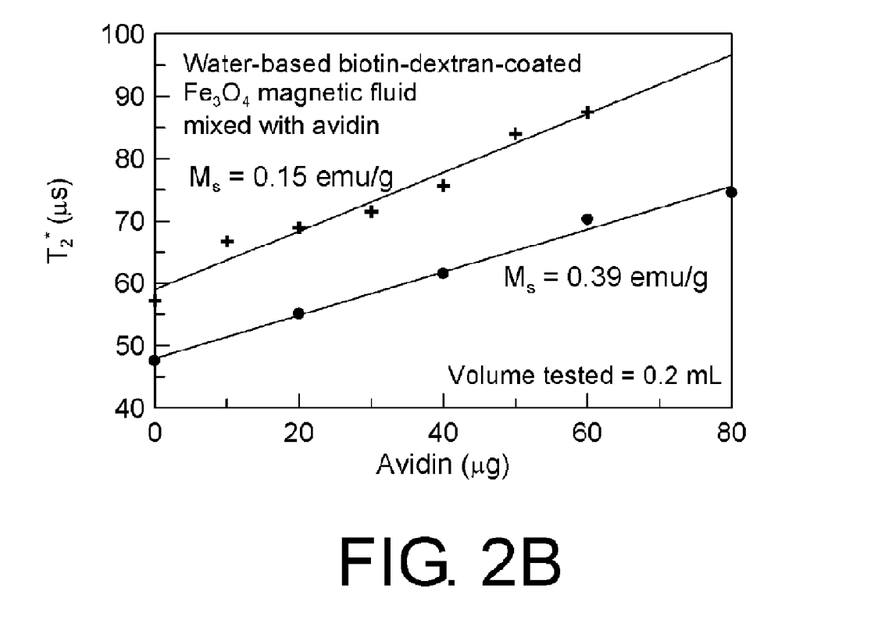
FIG. 2B shows the relationship of the relaxation time $T_2^*$ and the amount of avidin added in the magnetic fluid.

By way of adding various amounts of avidin into a control solution that includes magnetic nanoparticles coated with a fixed amount of the bioprobe and measuring the $T_2^*$ before and after adding avidin to the control solution, the relationship between the relaxation time $T_2^*$ of the solution and the amount of the added avidin can be obtained, as shown in FIG. 2B. FIG. 2B shows the relationship of the relaxation time $T_2^*$ and the amount of avidin added in the magnetic fluid for various concentrations of magnetic nanoparticles. Obviously, before using the magnetic fluid (the solution containing the bioprobe-coated magnetic nanoparticles) to measure the sample including unknown amounts of the bio-targets, it is necessary to establish the relationship between the relaxation time $T_2^*$ of the magnetic fluid and the amount of the bio-targets, where the magnetic fluid has a known amount of nanoparticles.

Figure 3A:
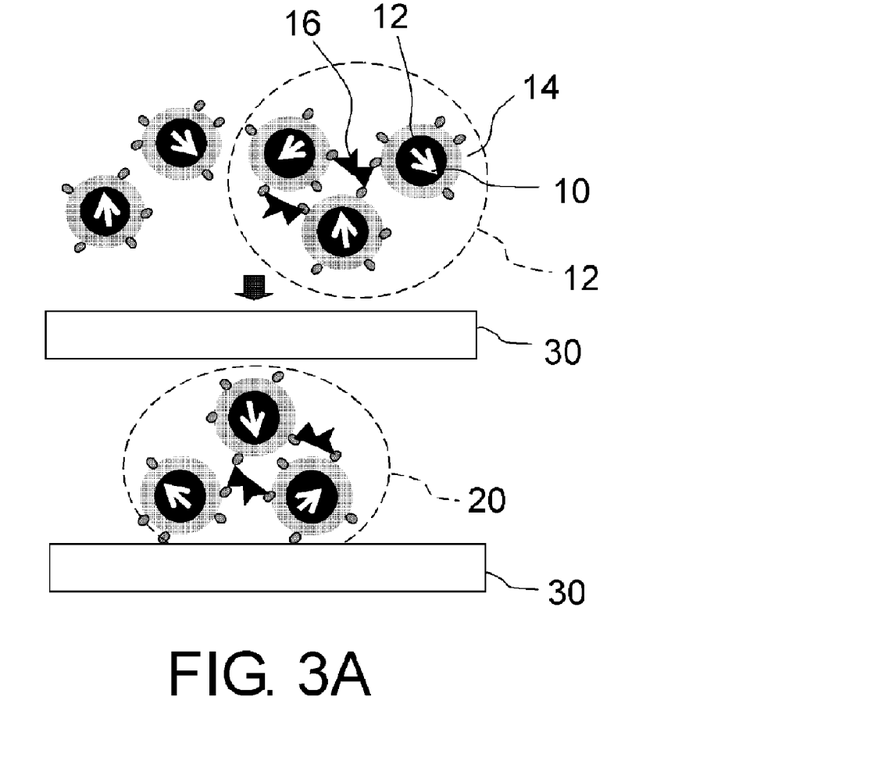
FIG. 3A is a schematic model for the filtration of the particles clusters.

As more bio-targets 16 are added into the magnetic fluid, more magnetic particle clusters 20 are formed. FIG. 3A is a schematic model for the filtration of the particles clusters. As shown in FIG. 3A, the particle clusters 20 can be separated from single magnetic nanoparticles 10 through filtration by a micro-filter 30. During filtration, the magnetic fluid along with bio-targets is filtrated through the micro-filter 30 and washed with a phosphate-buffered saline (PBS) solution. The micro-filter 30 is a non-magnetic film filter with a pore size of 30-130 nm, for example. The single magnetic nanoparticles 10, which have a diameter much smaller than the pore size, passed through the micro-filter 30, while the particle clusters 20 are remained on the non-magnetic micro-filter 30.

Since the amount of the added/detected bio-targets is directly related to the amount of formed particle clusters, the amount of the added bio-targets can be determined by measuring the amount of the magnetic particle clusters. After obtaining the particle clusters 20, the magnetization M of the particle clusters 20 is measured under different magnetic field in order to obtain the magnetic hysteresis curve of the particle clusters. The measurement can be performed to the particle clusters 20 with or without the non-magnetic micro-filter 30. For conveniences, it is preferable to measure the particle clusters 20 together with the micro-filter 30. In this embodiment, a superconductive quantum interference device (SQUID) gradiometer system was used to measure the magnetic hysteresis curve. However, other types of magnetometers or gradiometers can also be used.

Figure 3B:
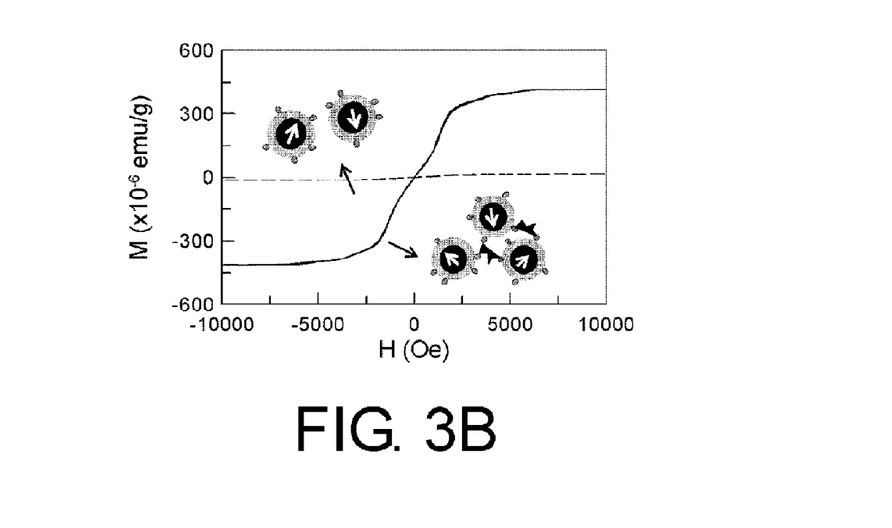
FIG. 3B shows the relationship of the magnetization M and the magnetic field H for the filtrated magnetic fluid and the magnetic particle clusters.

FIG. 3B shows the relationship of the magnetization M vs. the magnetic field H (i.e. the magnetic hysteresis curve), for the filtrated magnetic particle clusters using the biotin-avidin pair as an example. The dashed line in FIG. 3B denotes the magnetic hysteresis curve for the filtrated magnetic fluid without the addition of avidin, while the solid line denotes the magnetic hysteresis curve of the magnetic particle clusters (after addition of avidin).

It is found that the magnetization M of the particle clusters become saturated under high magnetic field. This saturated magnetization value is so-called saturated magnetization $M_s$. In FIG. 3B, it is observed that the magnetic hysteresis curve for the filtrated magnetic fluid without the addition of avidin has a very small saturated magnetization $M_s$. Theoretically, this $M_s$ value should be zero. However, due to the un-avoided problem in the synthesis process, very little amounts of large magnetic nanoparticles may remain in the fluid and lead to the non-zero $M_s$. On the other hand, the saturated magnetization $M_s$ of the magnetic hysteresis curve of the magnetic particle clusters is relatively large.

Figure 4:
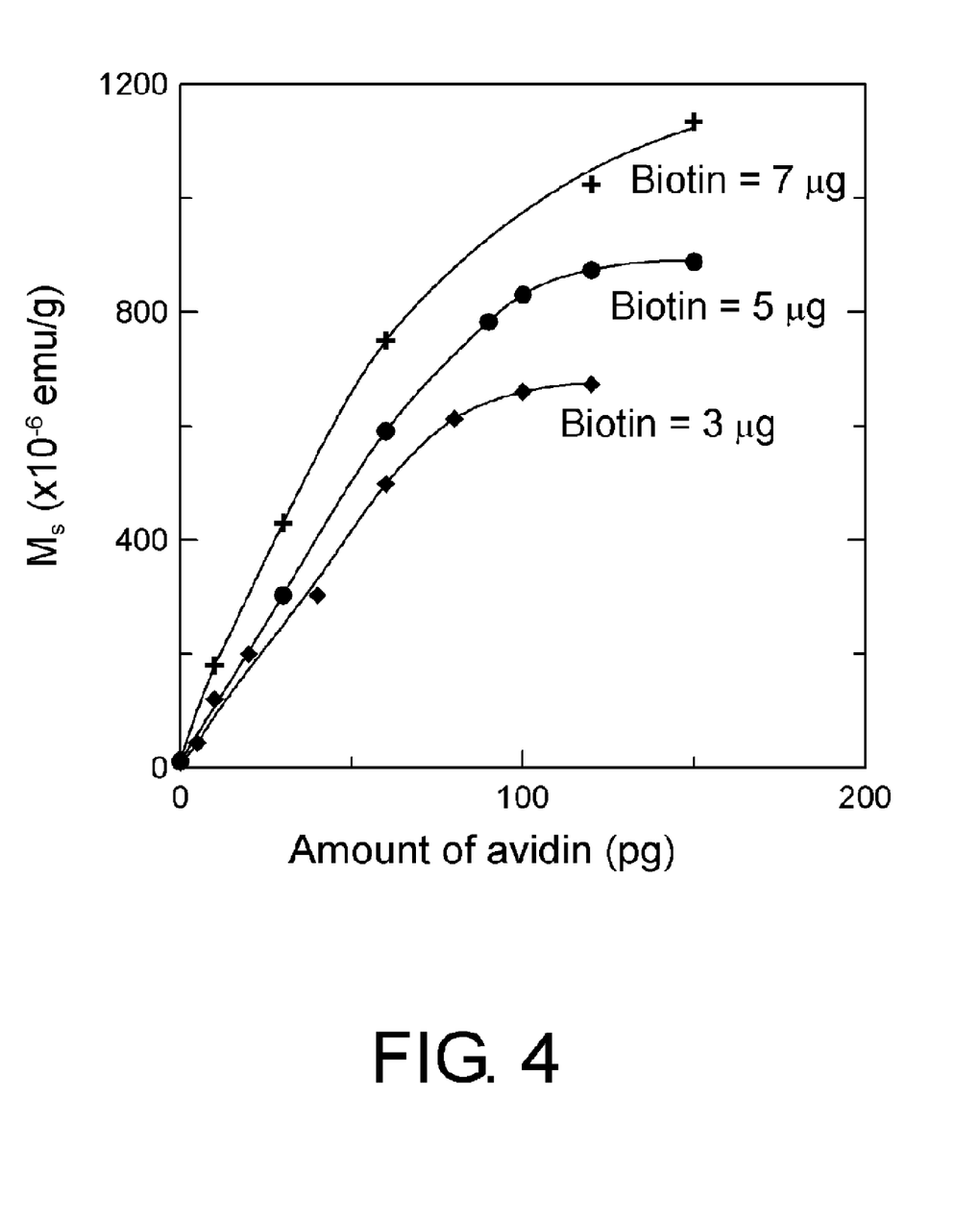
FIG. 4 shows the relationship of the saturated magnetization $M_s$ of the magnetic particle clusters and the added amounts of avidin in the solution.

Through measuring the magnetic hysteresis curve of the particle clusters, the saturated magnetization $M_s$ of the formed particle clusters can be obtained. By way of adding various amounts of avidin into a control solution that includes magnetic nanoparticles coated with a fixed amount of the bioprobe and measuring the $M_s$ for the formed particle clusters after adding avidin to the control solution, the relationship between the saturated magnetization of the resultant particle clusters and the amount of the added avidin can be obtained, as shown in FIG. 4. Obviously, before using the magnetic fluid (the solution containing the bioprobe-coated magnetic nanoparticles) to measure the sample including unknown amounts of the bio-targets, it is necessary to establish the relationship between the amount of the bio-targets and the saturated magnetization of the particle clusters from the control solution, where the nanoparticles are pre-coated with a known amount of bioprobes.

For a given amount of biotin (for example, 3 μg), the $M_s$ of the particle clusters increases substantially linearly with the increasing amount of avidin. It is noted that the detectable amount of avidin is in the order of magnitude of $10^{-12}$ g (pg) in 1-c.c. sample or in the concentration of pg/ml, demonstrating that it is a highly-sensitive detection method. In addition, as shown in FIG. 4, when the amount of avidin in the sample solution (1 ml) is below 80 pg, the $M_s$ is in the substantially linear range and resolvable. However, as the amount of avidin in the sample solution is higher than 80 pg, the $M_s$ remains almost unchanged. It is possible because that almost all the biotin molecules on the nanoparticles are bound to avidin molecules and no more particle clusters are formed even when more avidin is added to the magnetic fluid. Hence, the dynamic range of the assay using the magnetic fluid with 3-μg biotin was about 80 pg/ml for avidin. The dynamic range for detecting avidin can be expanded by using the magnetic fluid with larger amounts of biotin. As shown in FIG. 4, for the magnetic fluid with 7-μg biotin, resolvable $M_s$ can be measured for avidin in an amount up to 150 pg. Therefore, by adjusting the amount of the bioprobe bound to the magnetic nanoparticles (i.e. the initial amount of the bioprobe added to the solution), the appropriate range for detecting the bio-target can be controlled. Since the maximum amount of bioprobe is directly proportional to the amount of nanoparticles in the magnetic fluid, the appropriate range for detecting the bio-target can be controlled vice versa by varying the concentration of nanoparticles in the magnetic fluid.

Alternatively, the amount of the bio-target in the sample can be measured based on the changes in the alternating current (ac) magnetic susceptibility reduction.

As discussed above, the added bio-targets cause the agglomeration of the magnetic nanoparticles and result in the formation of magnetic particle clusters. On the other hand, if the magnetic fluid added with the bio-targets is not filtered by the micro-filter, magnetic particle clusters along with free magnetic nanoparticles exist in the solution when the added bio-targets are not in excess. When an external magnetic field is applied, the magnetic moments of single free nanoparticles and particle clusters are aligned along the external magnetic field. As the magnetic field is quenched, the single magnetic nanoparticles and particle clusters will relax with different relaxation behaviours. According to the reported data, the single magnetic nanoparticles show Brownian relaxation with a relaxation time constant of several microseconds, while the magnetic particle clusters exhibit Néel relaxation with a relaxation time constant of hundreds of milliseconds. Thus, under an external alternating current (ac) magnetic field with a frequency of several tens to $10^6$ Hz, only the magnetic moments of single magnetic nanoparticles are able to oscillate with the external ac magnetic field, while the magnetic moments of the particle clusters are almost held still. Hence, the ac magnetic susceptibility $X_{ac}$ of the solution is substantially attributed from the single magnetic nanoparticles, instead of the particle clusters. Therefore, the ac magnetic susceptibility $X_{ac}$ of the solution (magnetic fluid containing free magnetic nanoparticles) should become smaller after the addition of the bio-target. This is because more particle clusters are formed and less free magnetic nanoparticles exist in the solution. As a result, the amount of the bio-target (e.g. avidin) can be measured based on the reductions in the values of the ac magnetic susceptibility $X_{ac}$.

Figure 5:
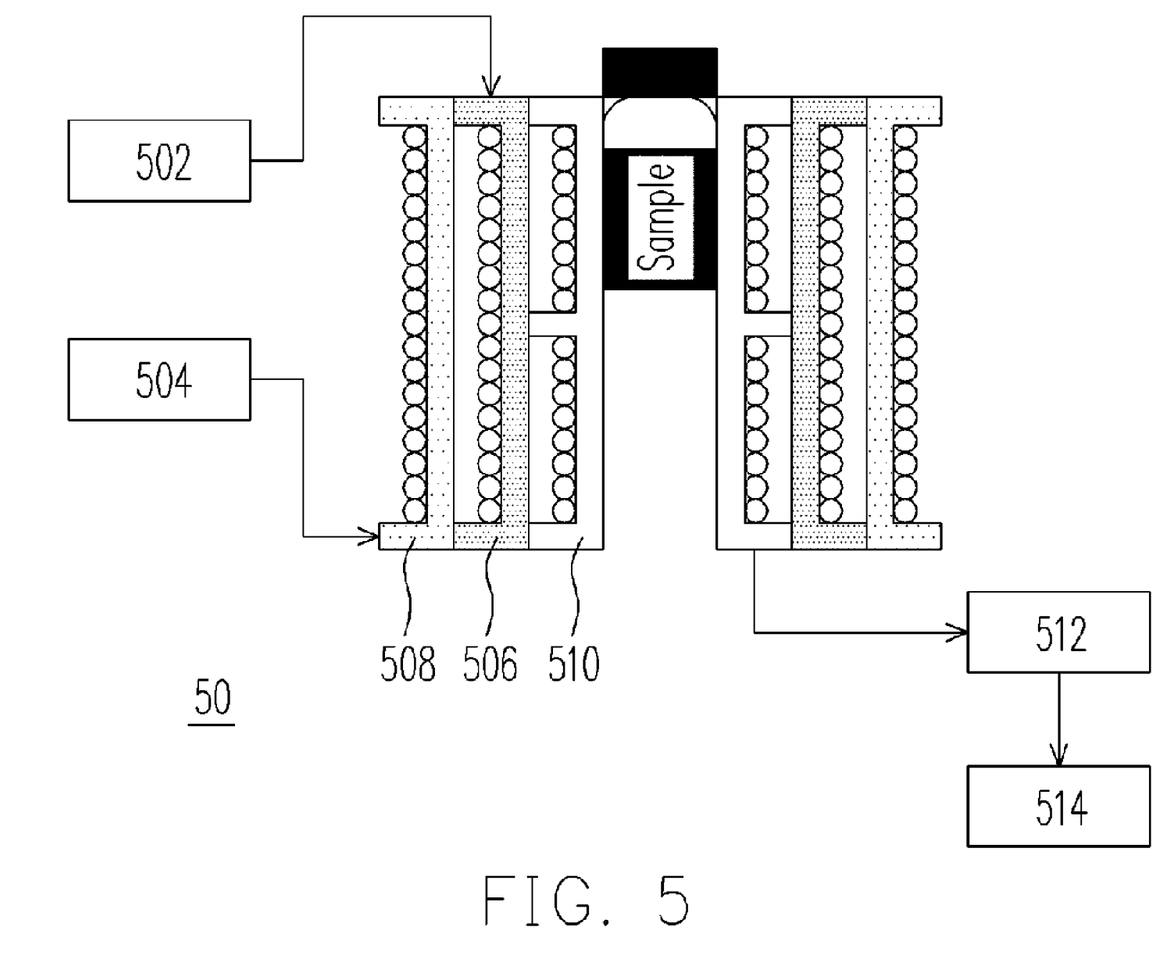
FIG. 5 is a schematic diagram of the measurement system suitable for ac magnetic susceptibility detection.

A novel system for measuring the ac magnetic susceptibility has been designed and assembled by the inventors of this application. FIG. 5 is a schematic diagram of the measurement system suitable for magnetic susceptibility detection. The system 50 comprises at least two function generators 502/504, two excitation coils 506/508, one pick-up coil 510, one read-out device 512 and a spectrum analyzer 514. The two function generators 502/504 provide two ac voltages of different frequencies ($f_1$ and $f_2$, which may range from several tens to $10^6$ Hz) to the two excitation coils 506/508, respectively. These two excitation coils 506/508 can respectively generate two ac magnetic fields with frequencies $f_1$ and $f_2$ to magnetize the sample. The ac magnetic susceptibility signal of the solution is detected by the pick-up call 510, and then filtered and amplified with the read-out device 512. The pick-up coil 510 consists of two solenoids in serious, but the wires of these two solenoids are wired in the opposite direction with each other. Then, the ac magnetic susceptibility signal is analyzed at a certain frequency ($mf_1+nf_2$) using the spectrum analyzer 514, where m and n are non-zero and positive integers. By measuring the ac magnetic susceptibility at the frequency ($mf_1+nf_2$) for the magnetic fluid added with various amounts of the bio-target (e.g. avidin), the relationship between the changes in the ac magnetic susceptibility and the amounts of the bio-target can be obtained.

Figure 6:
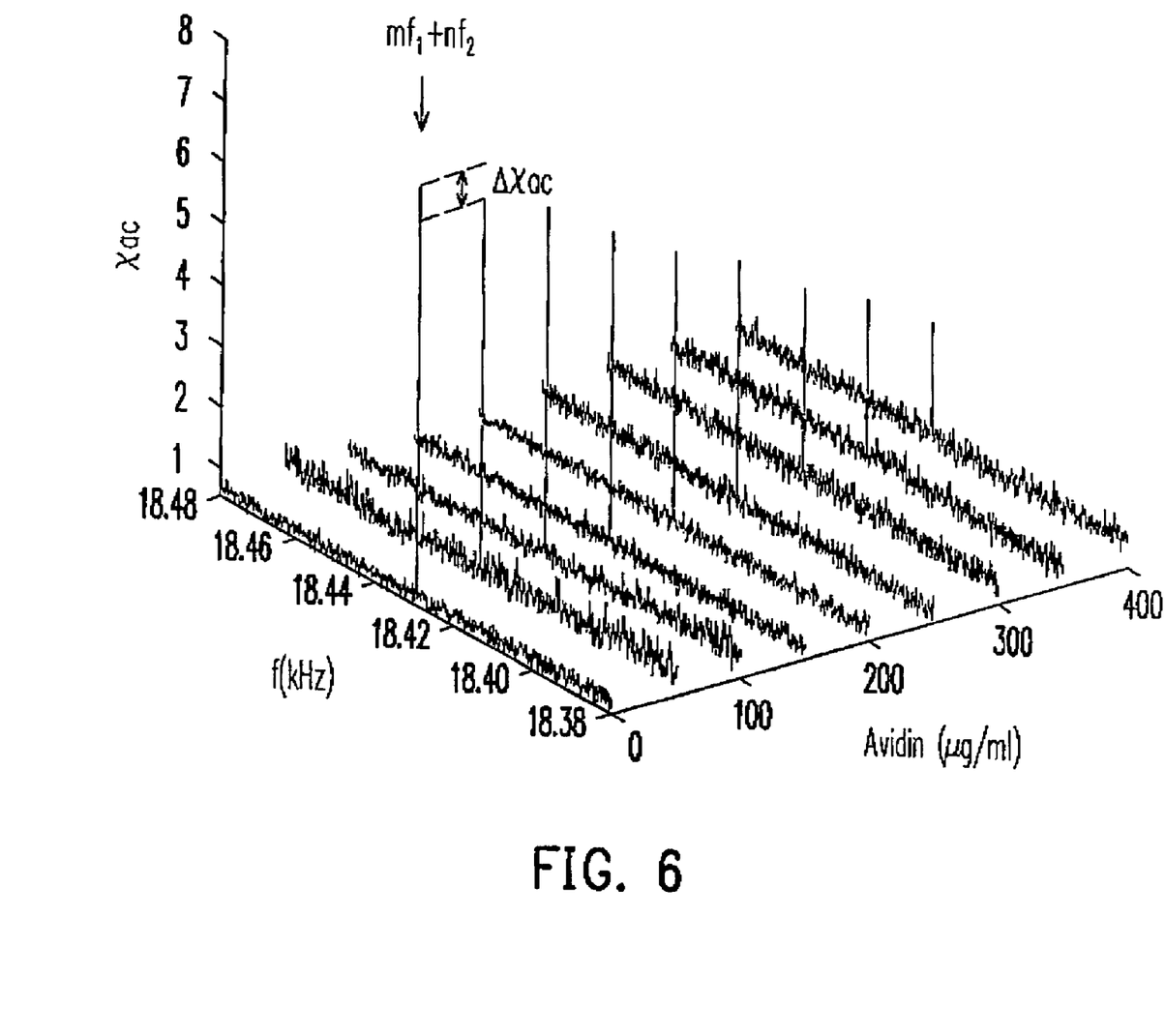
FIG. 6 shows the measured frequency spectra of the ac magnetic susceptibility $X_{ac}$ of the magnetic solution for various amounts of avidin.
Figure 7:
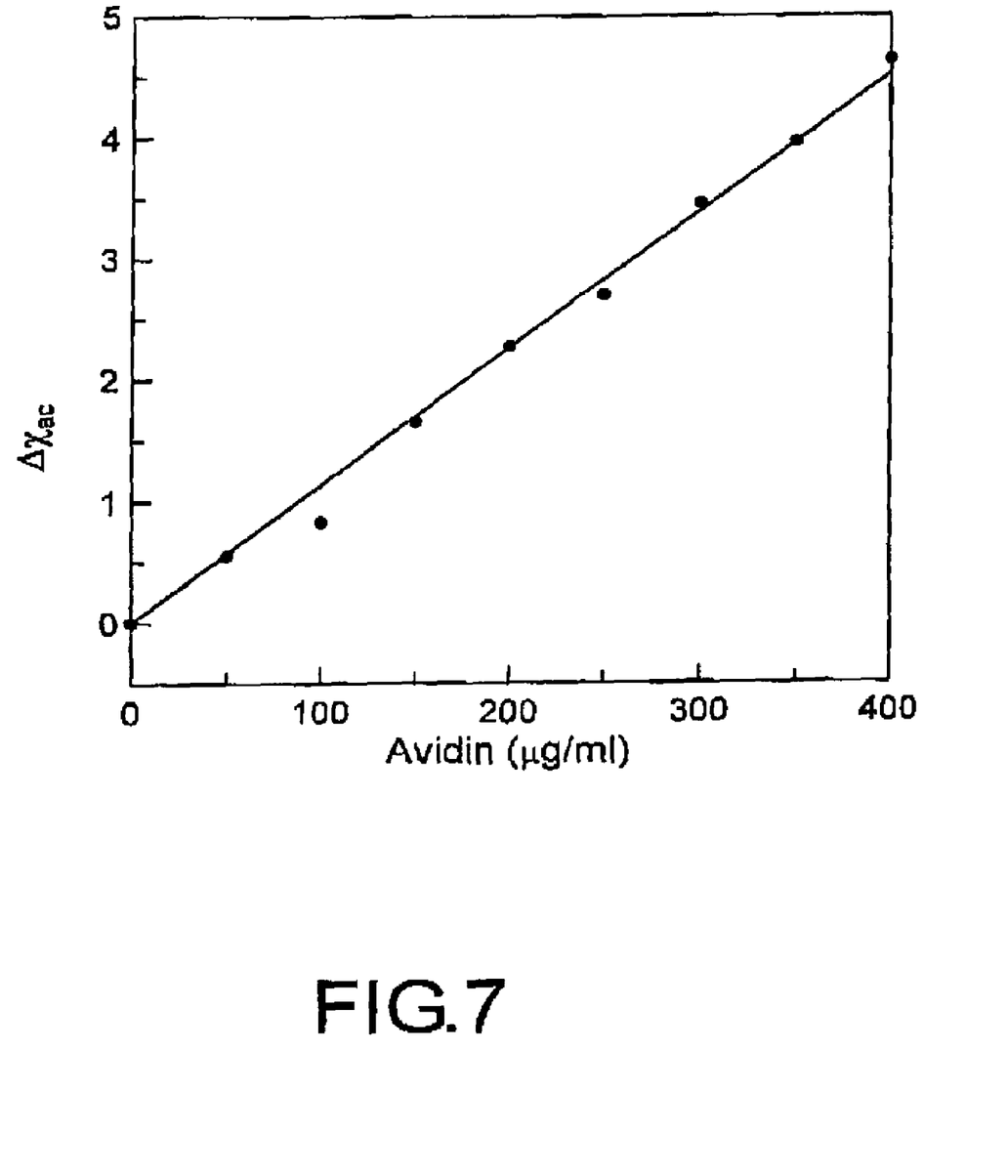
FIG. 7 shows the relationship of the obtained ac magnetic susceptibility reductions ($\Delta X_{ac}$) and the amounts of avidin.

FIG. 6 shows the measured frequency spectra of the ac magnetic susceptibility $\chi_{ac}$ for the solution (in a fixed volume of 1 ml) added with various amounts of avidin. The ac magnetic susceptibility $\chi_{ac}$ decreases as the amount of avidin increases. It is noted that if the amount of added avidin (bio-target) is excess in comparison with the biotin (bio-probe), a saturated $\chi_{ac}$ should be obtained. The ac magnetic susceptibility reduction ($\Delta\chi_{ac}$) between the ac magnetic susceptibility of the solution (magnetic fluid) without avidin and the solution added with a specific amount of avidin can be obtained from the results in FIG. 6. The relationship of the obtained ac magnetic susceptibility reductions ($\Delta\chi_{ac}$) and the amounts of avidin is shown in FIG. 7. Using the biotin-avidin pair as an example, a linear relationship is obtained between the $\Delta\chi_{ac}$ and avidin in an amount from zero to about 400 μg/ml. This indicates a very large dynamic range (detectable range) for detecting the amounts of the bio-target. Similarly, before using the magnetic fluid to measure the sample including unknown amounts of the bio-targets, it is necessary to establish the relationship between the amount of the bio-targets and the ac magnetic susceptibility reduction ($\Delta\chi_{ac}$) from the control solution, by adding various amounts of the bio-target in the control solution that includes magnetic nanoparticles coated with a fixed amount of the bioprobe and obtaining the $\Delta\chi_{ac}$ by measuring the $\chi_{ac}$ before and after adding the bio-target to the control solution.

Figure 8A:
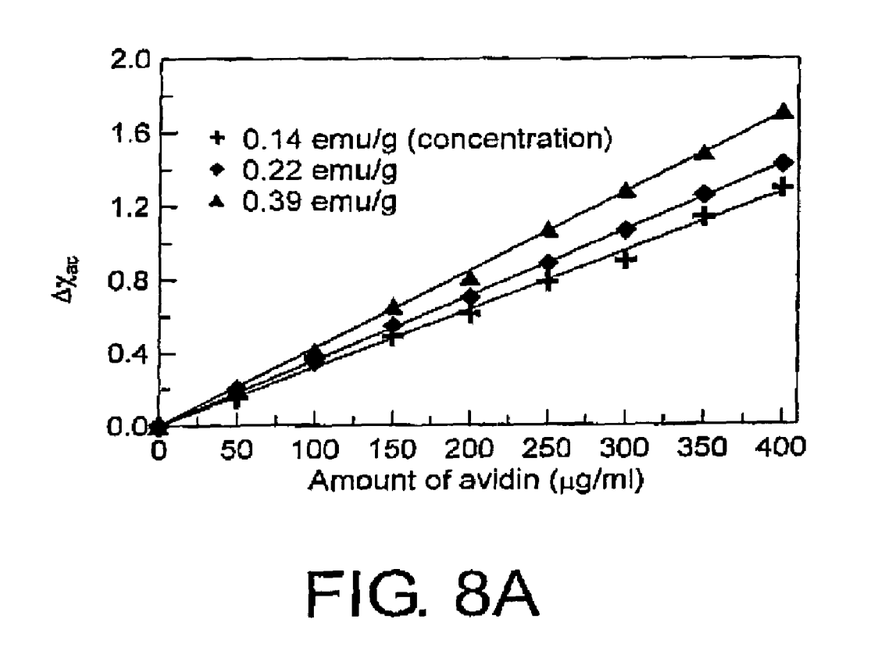
FIG. 8A shows the relationship of the obtained ac magnetic susceptibility reductions ($\Delta X_{ac}$) and the amounts of avidin for various concentrations of magnetic nanoparticles.
Figure 8B:
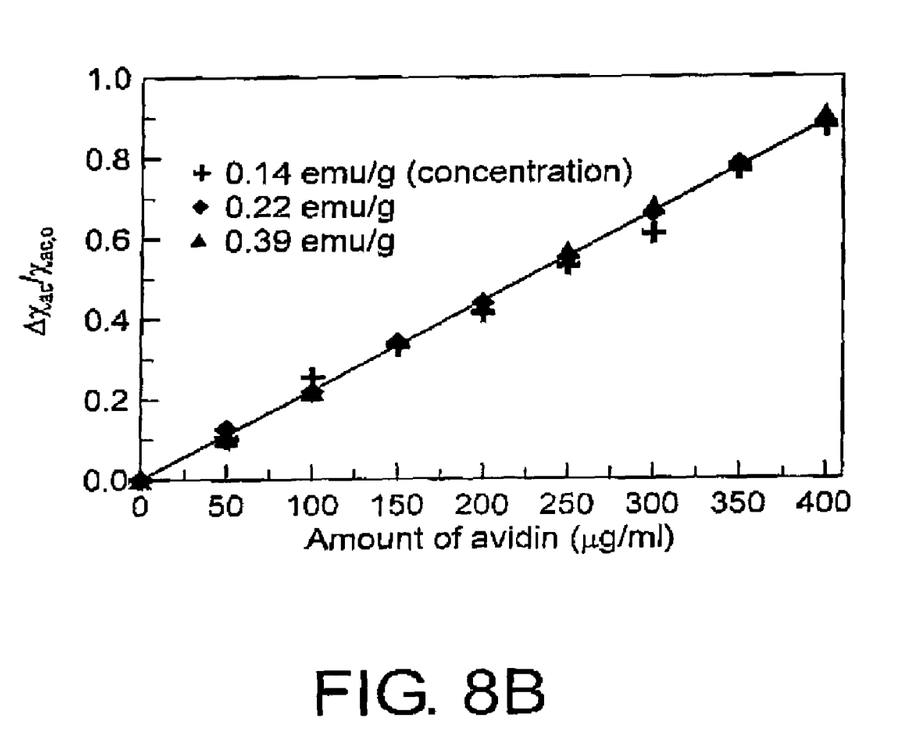
FIG. 8B shows the relationship of the normalized ac magnetic susceptibility reductions ($\Delta X_{ac}/X_{ac,o}$) and the amounts of avidin for various concentrations of magnetic nanoparticles.

FIG. 8A shows the relationship of the obtained ac magnetic susceptibility reductions and the amounts of avidin for various concentrations of magnetic nanoparticles. FIG. 8B shows the relationship of the normalized ac magnetic susceptibility reductions and the amounts of avidin for various concentrations of magnetic nanoparticles. The different curves shown in FIG. 8A represent the relationship for the magnetic nanoparticles in various concentrations. However, for the magnetic fluid having various concentrations of magnetic nanoparticles, a general curve can be obtained (as shown in FIG. 8B) by normalizing the ac magnetic susceptibility reduction $\Delta X_{ac}$ to the value of the ac magnetic susceptibility $X_{ac,o}$ of the sample without adding bio-targets. Therefore, in addition to the relationship of the ac magnetic susceptibility reduction and the amount of bio-targets, the relationship of the normalized ac magnetic susceptibility reduction and the amount of bio-targets is also useful.

Clearly, because the principles of the measuring methods proposed in this invention are based on magnetic properties of the magnetic fluid and/or the formed particle clusters, no fluorescence labels or coloring agents are required for determining the amount of the biomolecules (analytes) in the sample. Hence, no extra processing steps and less human labor are needed and the costs of the test assays can be reduced.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method of quantitatively measuring an amount of biomolecules in a sample comprising:

providing a solution having magnetic nanoparticles;

coating bioprobe molecules to surfaces of the magnetic nanoparticles in the solution;

measuring a first alternating current (ac) magnetic susceptibility of the solution at a mixture frequency ($mf_1+nf_2$), wherein m or n is independently an integer larger than zero, $f_1$ is integral times of $f_2$;

adding a sample containing the biomolecules to be detected to the solution, so that the biomolecules in the sample conjugate with the bioprobe molecules coated on the nanoparticles;

measuring a second ac magnetic susceptibility of the solution at the mixture frequency ($mf_1+nf_2$) after adding the sample, so as to obtain an ac magnetic susceptibility reduction at the mixture frequency ($mf_1+nf_2$) between the first and the second magnetic susceptibility to determine the amount of the biomolecules.

2. The method according to claim 1, further comprising establishing a relationship between the ac magnetic susceptibility reductions and amounts of the biomolecules by adding various amounts of the biomolecules to a control solution that includes magnetic particles coated with a fixed amount of bioprobes, and measuring the ac magnetic susceptibility reductions of the control solution.

3. The method according to claim 2, further comprising comparing the magnetic susceptibility reduction at the mixture frequency ($mf_1+nf_2$) of the sample with the established relationship obtained from the control solution and determining the amount of the biomolecules in the sample based on the established relationship.

4. The method according to claim 1, further comprising establishing a relationship between a normalized ac magnetic susceptibility reduction and amounts of the biomolecules by adding various amounts of the biomolecules to a control solution that includes magnetic particles coated with a fixed amount of bioprobes, measuring the ac magnetic susceptibility reduction of the control solution and normalizing the ac magnetic susceptibility reduction of the control solution.

5. The method according to claim 4, further comprising comparing the magnetic susceptibility reduction at the mixture frequency ($mf_1+nf_2$) of the sample with the established relationship obtained from the control solution and determining the amount of the biomolecules in the sample based on the established relationship.

6. The method according to claim 1, wherein a frequency range for the ac magnetic susceptibility is from $10^1$ to $10^6$ Hz.

7. The method according to claim 1, wherein the biomolecule is selected from the group consisting of carcinoembryonic antigen (CEA), α-fetoprotein (AFP), vascular cell adhesion molecule-1 (VACM-1), HBc, C-reactive protein (CRP), immunoglobulin G (IgG) and avidin.

8. The method according to claim 1, wherein the magnetic nanoparticles are $Fe_3O_4$ magnetic nanoparticles.

9. The method according to claim 8, wherein a diameter of the $Fe_3O_4$ magnetic nanoparticles is between about 25 nm to about 90 nm.

* * * * *